United States Patent
Nahhas

(10) Patent No.: US 8,128,675 B2
(45) Date of Patent: Mar. 6, 2012

(54) COOLING APPARATUS AND METHOD FOR REDUCING RISK OF MALE INFERTILITY IN HEATED ENVIRONMENTS

(76) Inventor: Fathallah Nahhas, Haifa (IL)

( * ) Notice: Subject to any disclaimer, the term of this patent is extended or adjusted under 35 U.S.C. 154(b) by 998 days.

(21) Appl. No.: 11/878,640

(22) Filed: Jul. 25, 2007

(65) Prior Publication Data

US 2008/0027383 A1     Jan. 31, 2008

Related U.S. Application Data

(60) Provisional application No. 60/907,569, filed on Apr. 9, 2007, provisional application No. 60/833,270, filed on Jul. 26, 2006.

(51) Int. Cl.
*A61F 7/00* (2006.01)
*A41B 9/00* (2006.01)
*A41B 9/02* (2006.01)

(52) U.S. Cl. ........ 607/104; 607/107; 607/108; 607/112; 2/400; 2/403; 2/404; 2/405

(58) Field of Classification Search ...... 2/400, 403–405; 607/104, 107
See application file for complete search history.

(56) References Cited

U.S. PATENT DOCUMENTS

| | | | | |
|---|---|---|---|---|
| 3,452,812 A * | 7/1969 | Betts | ............................... | 165/46 |
| 4,253,464 A * | 3/1981 | Zorgniotti et al. | ............ | 607/104 |
| 4,471,772 A | 9/1984 | Miller, Jr. | | |
| 5,243,974 A * | 9/1993 | Allen | ............................ | 607/108 |
| 5,628,769 A * | 5/1997 | Saringer | ........................ | 607/98 |
| 5,716,319 A * | 2/1998 | Sembert | ........................ | 600/38 |
| 5,871,526 A * | 2/1999 | Gibbs et al. | .................... | 607/104 |
| 6,068,607 A * | 5/2000 | Palmer et al. | .................... | 602/67 |
| 6,254,613 B1 * | 7/2001 | Harrison | ....................... | 606/118 |
| 6,308,341 B1 * | 10/2001 | Shelton | ............................ | 2/400 |
| 6,438,964 B1 | 8/2002 | Giblin | | |
| 6,665,877 B1 * | 12/2003 | Gray | ................................ | 2/69 |

(Continued)

FOREIGN PATENT DOCUMENTS

GB     2059265     4/1981

(Continued)

OTHER PUBLICATIONS

Response Dated Sep. 19, 2011 to Supplementary European Search Report and the European Search Opinion of Mar. 4, 2011 From the European Patent Office Re. Application No. 07789989.6.

(Continued)

*Primary Examiner* — Roy Gibson
*Assistant Examiner* — Kaitlyn Smith

(57) ABSTRACT

Cooling apparatus (and method) for reducing the risk of, and/or alleviating, male infertility, particularly in a heated environment, includes: a pouch to enclose the scrotal area of the male user; a thermoelectric cooling device to be worn by the male user at a distance from the pouch; and a fluid pump also to be worn by the male user for pumping a cooling fluid from the cold side of the thermoelectric cooling device to the pouch, and a cooling fluid over the hot side of the thermoelectric cooling device to dissipate the heat generated therein to the atmosphere. The thermoelectric cooling device and pump are incorporated in a waistband to be worn around the waist of the male user.

13 Claims, 5 Drawing Sheets

U.S. PATENT DOCUMENTS

| | | | |
|---|---|---|---|
| 6,770,058 B1* | 8/2004 | Liprie | 604/264 |
| 7,000,682 B2* | 2/2006 | Chambers | 165/46 |
| 2005/0193742 A1* | 9/2005 | Arnold | 62/3.5 |
| 2006/0235497 A1* | 10/2006 | Zanotti | 607/104 |
| 2008/0046047 A1* | 2/2008 | Jacobs | 607/108 |
| 2008/0306433 A1* | 12/2008 | Cesaroni | 604/23 |
| 2010/0094386 A1* | 4/2010 | Margolis et al. | 607/108 |

FOREIGN PATENT DOCUMENTS

| | | |
|---|---|---|
| WO | WO 98/23235 | 6/1998 |
| WO | WO 01/59372 | 8/2001 |
| WO | WO 2004/111741 | 12/2004 |
| WO | WO 2008/012819 | 1/2008 |

OTHER PUBLICATIONS

Communication Pursuant to Rules 70(2) and 70a(2) EPC Dated Mar. 22, 2011 From the European Patent Office Re. Application No. 07789989.6.

Supplementary European Search Report and the European Search Opinion Dated Mar. 4, 2011 From the European Patent Office Re. Application No. 07789989.6.

International Search Report Dated Sep. 22, 2008 From the International Searching Authority Re.: Application No. PCT/IL07/00934.

Written Opinion Dated Sep. 22, 2008 From the International Searching Authority Re.: Application No. PCT/IL07/00934.

Communication Pursuant to Article 94(3) EPC Dated Oct. 12, 2011 From the European Patent Office Re. Application No. 07789989.6.

* cited by examiner

COOLING APPARATUS AND METHOD FOR REDUCING RISK OF MALE INFERTILITY IN HEATED ENVIRONMENTS

RELATED APPLICATIONS

This application claims the benefit of U.S. Provisional Patent Applications Nos. 60/833,270 filed Jul. 26, 2006 and 60/907,569 filed Apr. 9, 2007, the contents of which are incorporated herein by reference.

FIELD AND BACKGROUND OF THE INVENTION

The present invention relates to cooling apparatus, and also to a cooling method, for reducing the risk of, and/or alleviating, male infertility in heated environments.

Temporary or permanent infertile marriages are, in many cases, attributable to poor male semen quality emanating from prolonged exposures of the scrotal area, and the testicles in particular, to elevated temperatures. This condition, termed varicocele, may be alleviated by surgical intervention, called varicocelectomy, a procedure in which inflated veins are sutured. This procedure has a success rate of about 40%; in addition, it may have to be repeated in case a varicocele-relating poor semen condition recurs. Another common method of treatment of this condition is assisted reproduction.

An alternative, noninvasive method of treatment involves the systematic and controlled lowering of the temperature to which the scrotal area is exposed. Experience shows that prolonged reduction of the temperature of the scrotal area by about 3-5° C., may be effective in reversing male infertility to the extent that conception could be achieved, thus obviating the need for surgical or other interventions.

In the past, various means and devices have been proposed to achieve scrotal cooling. These include:

(1) disposable devices containing endothermic chemical compounds which absorb heat by a produced chemical reaction and thereby are capable of diminishing local temperatures for the limited duration of the reaction; these devices, however, require frequent replacement of the chemical compounds and lack basic control capabilities; and (2) devices utilizing the latent heat of vaporization of an evaporative liquid, or the latent heat of liquefaction of a liquefying solid; these devices, however, also require frequent recharging and replacement of the spent materials and also lack basic control capabilities.

Also known are devices with electrically-driven cooling sources, e.g., Peltier thermoelectric units, for cooling the head or other body parts, which devices usually present cooling surfaces in direct contact with the body area to be cooled. These devices, although inherently possessing control capabilities, require heat dissipation in immediate proximity to the treated areas, which renders them unsuitable for treating those body areas which are traditionally covered with clothes, e.g., the scrotal area.

OBJECTS AND BRIEF SUMMARY OF THE PRESENT INVENTION

An object of the present invention is to provide cooling apparatus, and also a cooling method, having advantages in one or more of the above respects when used for cooling the scrotal area in order to reduce the risk of, and/or alleviate, male infertility.

According to one aspect of the present invention, there is provided cooling apparatus for reducing the risk of male infertility, particularly in a heated environment, comprising:

a waistband to be worn around the waist of the male user;

a pouch carried by said waistband, said pouch being configured and dimensioned to enclose the scrotal area of the male user;

a thermoelectric cooling device carried by said waistband, said thermoelectric cooling device having a cold side and a hot side and fluid pumping means carried by said waistband for pumping a first fluid through a cooling path across said cold side of said thermoelectric cooling device to said pouch to cool said pouch and the scrotal area enclosed thereby, and a second fluid through a heat-dissipation path across said hot side of the thermoelectric cooling device to an outlet from said waistband remotely located from said pouch to thereby dissipate the heat produced by said thermoelectric cooling device in cooling said pouch at a location remote from said pouch.

In the preferred embodiments of the invention described below, said waistband includes a front side carrying said thermoelectric cooling device and said pouch spaced below said thermoelectric cooling device, and a back side in which said outlet of the heat-dissipation path is located.

In one described preferred embodiment, a fan carried by the front side of the waistband dissipates the heat from the front side at a distance from the pouch; and in another described embodiment, the waistband includes an air channel leading to the atmosphere from the back side of the waistband for dissipating the heat from the back side at an even further distance from the pouch.

A still further embodiment is described, wherein the fluid pump is a fan, or air pump, which drives ambient air through a cooling path including the cold side of the thermoelectric cooling device and the pouch to the atmosphere, and also through a heat-dissipation path including the hot side of the thermoelectric cooling device directly to the atmosphere.

In all the described embodiments, the waistband further carries a battery for powering the thermoelectric cooling device, and a controller for controlling the thermoelectric cooling device; also the thermoelectric cooling device is a Peltier device.

According to another aspect of the present invention, there is provided apparatus for reducing the risk of, and/or alleviating, male infertility in a heated environment, comprising: a waistband to be worn around the waist of the male user; a pouch carried by said waistband, said pouch being configured and dimensioned to enclose the scrotal area of the male user; a thermoelectric cooling device carried by said waistband, said thermoelectric cooling device having a cold side and a hot side; and fluid pumping means carried by said waistband for pumping a first fluid through a cooling path across said cold side of said thermoelectric cooling device to said pouch to cool said pouch and the scrotal area enclosed thereby, and a second fluid through a heat-dissipation path across said hot side of the thermoelectric cooling device to dissipate the heat produced by said thermoelectric device in cooling said pouch.

As will be described more particularly below, such a cooling apparatus and method enable achieving a number of important advantages over the prior art, including some or more of the following:

(1) Heat rejection from the Peltier unit to the environment is done distally from the treated (scrotal) area thus avoiding the problem inherent in similar devices which do not dissipate the generated heat at a location distant from the treated area.

(2) The device requires infrequent electrical rechargings, which are relatively simple and non-expensive.

(3) A replacement, rechargeable DC power source may be used which could be recharged at a convenient time.

(4) The device can be operated directly on the mains line when mobility of the user is not required.

(5) The device can be controlled by a microprocessor which facilitates precise and stable thermal conditions at the treated area, controls condensation in high humidity climatic conditions, facilitates direct fine control by the user, and minimizes energy consumption.

(6) The device is portable and is lightweight, and when carried on a waist belt, attracts minimal attention.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Figure 1:
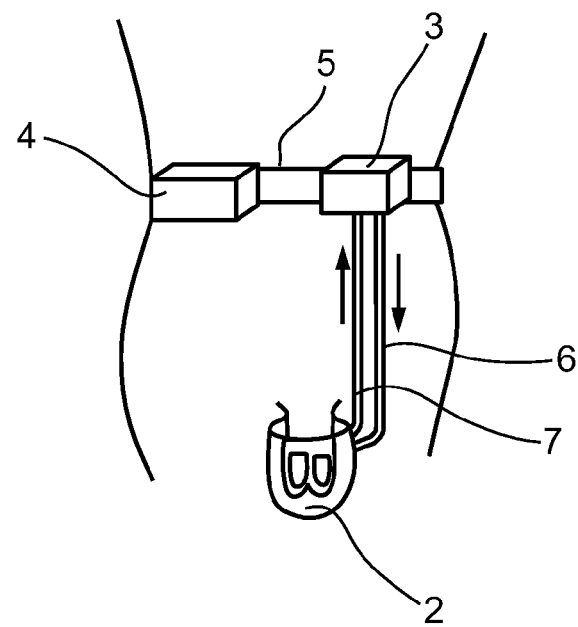
FIG. 1 schematically illustrates one form of cooling apparatus constructed in accordance with the present invention.

FIG. 1 schematically illustrates cooling apparatus constructed in accordance with the present invention as including: a pouch 2 configured and dimensioned to enclose the scrotal area of a male user; a cooling unit 3 including a thermoelectric cooling device, coolant liquid such as water, and a liquid pump for cooling pouch 2; and a powering unit 4 including a rechargeable power supply and a controller for controlling operation of the pump and the cooling device within cooling unit 3. All the foregoing units are carried by a waistband 5 to be worn around the waist of the male user, with the pouch 2 depending below the waistband. The cooling unit 3 supplies the coolant liquid to the pouch 2 via a flexible feed conduit 6, and returns the liquid back to the cooling unit 3 via a flexible drain conduit 7.

Figure 2:
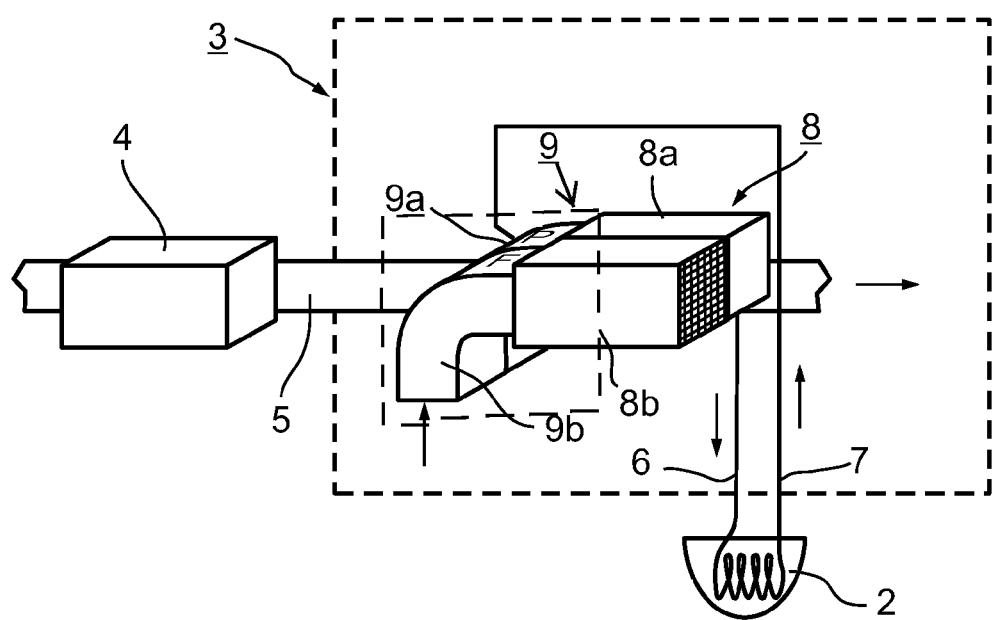
FIG. 2 more particularly illustrates the construction of the cooling apparatus of FIG. 1.

FIG. 2 more particularly illustrates the construction of the cooling unit 3 of FIG. 1. As shown FIG. 2, cooling unit 3 includes a thermoelectric cooling device, generally designated 8, having a cold side 8a and a hot side 8b, energized and controlled by the power supply unit 4. Cooling unit 3 further includes fluid pumping means, generally designated 9, including a liquid pump 9a for circulating a cooling liquid through a first path including the cold side 8a of thermoelectric cooling device 8, feed conduit 6 to the inlet side of pouch 2, and drain conduit 7 from the outlet side of the pouch and back to the inlet side of liquid pump 9a. Fluid pumping means 9 further include a fan 9b for driving ambient air from the atmosphere through the hot side 8b of thermoelectric cooling device 8 and directly back to the atmosphere, in order to dissipate the heat generated in the hot side 8b, as shown by the arrows in FIG. 2.

Figure 3:
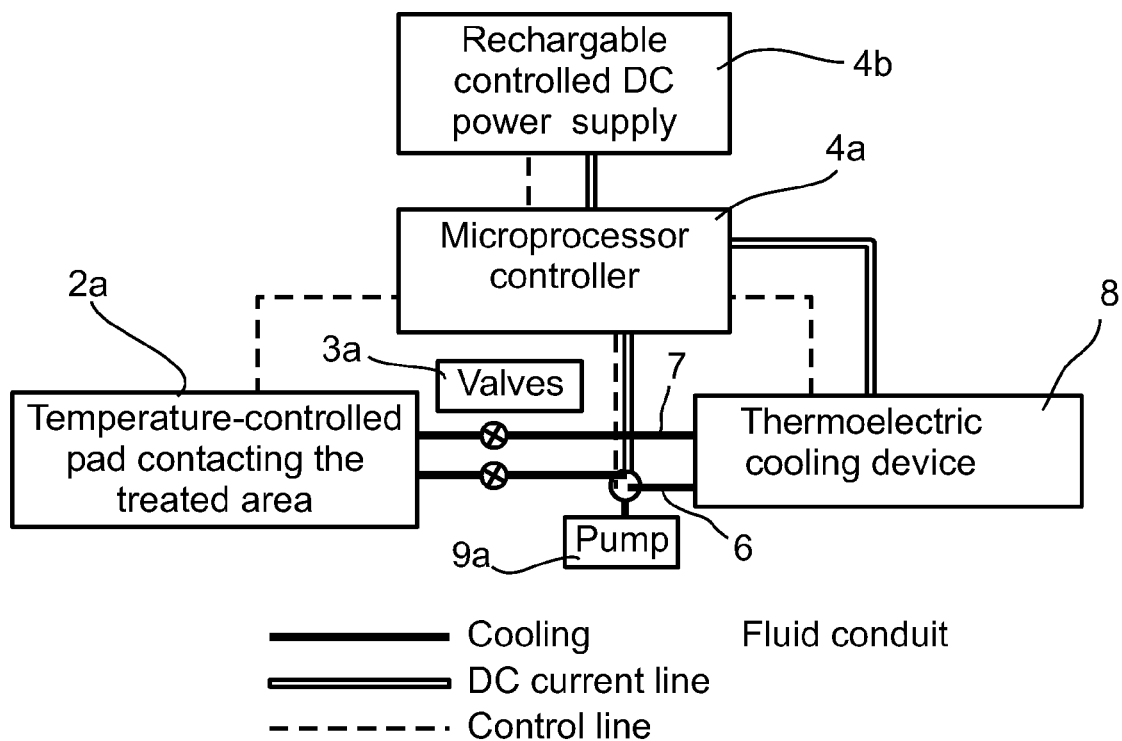
FIG. 3 is a block diagram illustrating the apparatus of FIG. 1.

FIG. 3 is a block diagram schematically illustrating the main functional components in the cooling apparatus of FIG. 1. Thus, block 2a indicates a temperature-controlled pad contacting, or otherwise exposed to, the treated area (the scrotal area of the male user) which pad is within pouch 2 of FIG. 1. The thermoelectric cooling device indicated by block 8, the liquid pump indicated by block 9a, and the valves indicated by block 3a, are within the cooling unit 3 of FIG. 1. The microprocessor of block 4a, and the rechargeable controlled DC power supply of block 4b, are within the powering unit 4 of FIG. 1. FIG. 2 further shows the supply conduit 6 from the cooling unit 3 to the pouch 2, and the feed conduit 7 from the pouch back to the cooling unit.

For simplicity purposes, the block diagram of FIG. 3 does not show the fan 9b for dissipating directly to the atmosphere the heat from the hot side 8b of the thermoelectric cooling device 8.

Liquid pump 9a illustrated in FIG. 2, as well as the liquid pump illustrated in the further embodiments described below, may be a miniature gear pump which can be of a very compact size and operates on 6-12 volts DC.

Figure 4:
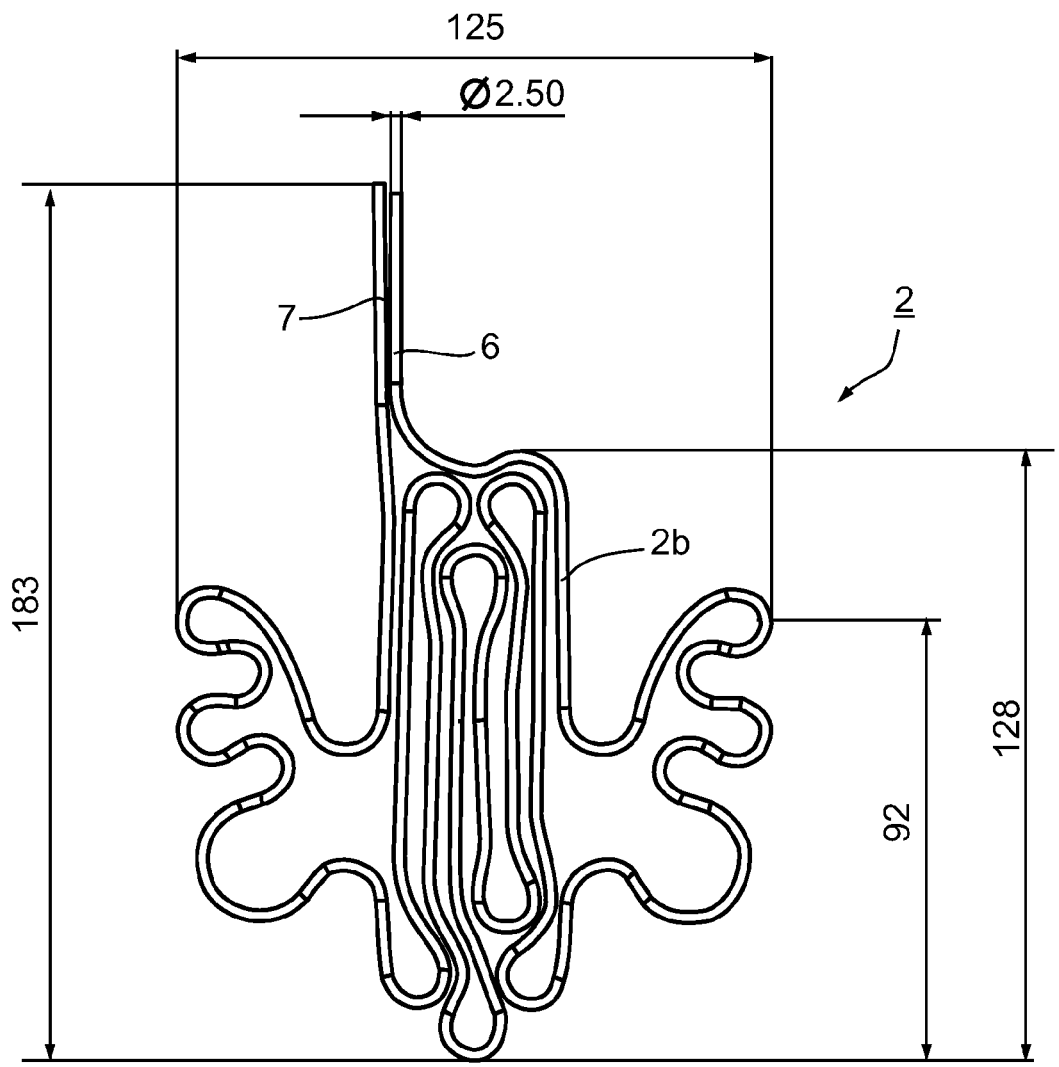
FIG. 4 illustrates an example of the cooling fluid conduit in the pouch of FIG. 1.

FIG. 4 illustrates one example of the water conduit 2b that may be included in pad 2a of pouch 2. As shown in FIG. 2, conduit 2b is connected to the outlet side of the cooling device 8a by the feed conduit 6, and by the drain conduit 7 back to the inlet side of the liquid pump 9a. Water conduit 2b is of a long winding configuration so as to traverse substantially the complete surface area of the pouch 2 through which the cooling liquid is circulated. FIG. 4 illustrates an example of preferred dimensions (in mm) which may be used for conduit 2b.

Figure 5:
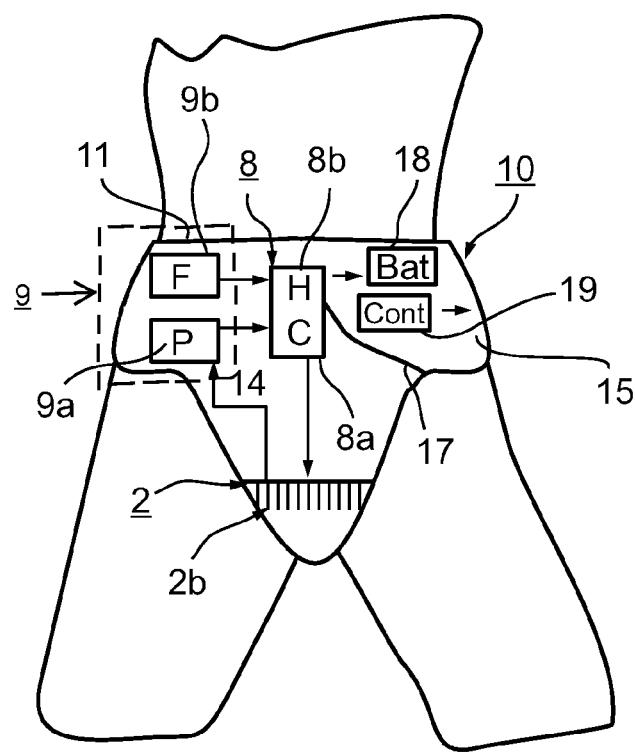
FIGS. 5, 6 and 7 are front, side and rear views, respectively, illustrating another form of cooling apparatus constructed in accordance with the present invention incorporated in a jockstrap type of undergarment.
Figure 6:
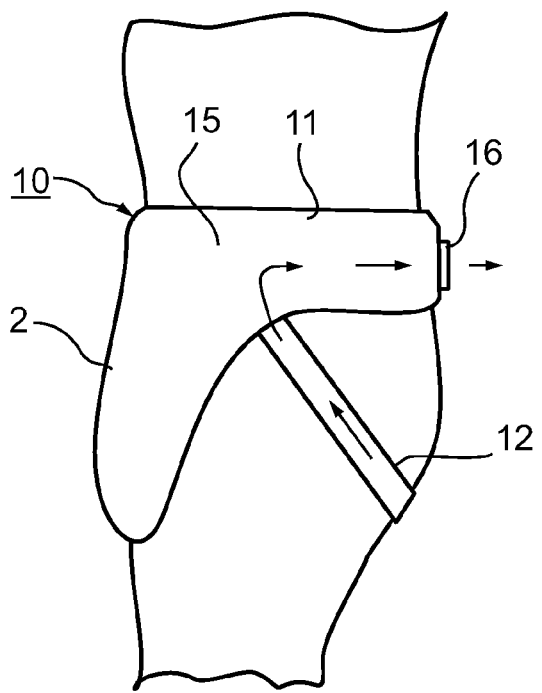
Figure 7:
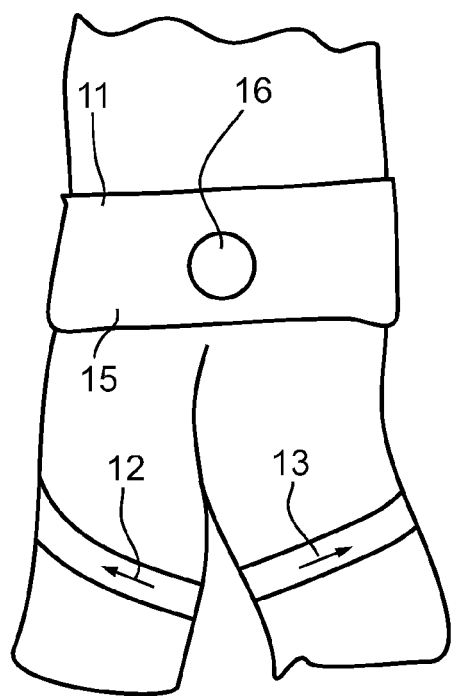

FIGS. 5-7 illustrate an example of one implementation of the cooling system of FIGS. 1-3 in the form of an undergarment to produce a light, portable device which is convenient to wear and to use. In the example of FIGS. 5-7, the undergarment, therein generally designated 10, is a jockstrap. It includes a waistband 11 secured at its front side to the upper end of pouch 2. Jockstrap 10 further includes two leg straps 12, 13, secured at one of their ends to the lower end of pouch 2, and at their opposite ends to the opposite sides of waistband 11.

As shown particularly in FIG. 5, waistband 11 includes the thermoelectric cooling device 8 which has a cold side 8a communicating with the pouch, and a hot side 8b exposed to the atmosphere and facing away from the pouch. Waistband 11 further carries the liquid pump 9a for pumping a cooling liquid, such as water, through a first conduit 14 between the outlet side of liquid pump 9a and the cold side 8a of the thermoelectric cooling device 8, the feed conduit 6 from the cold side 8a of the thermoelectric cooling device 8 and the inlet to conduit 2b within the pouch 2; and the drain conduit 7 from the outlet of conduit 2b to the inlet side of the liquid pumping device 9a.

Fan 9b, which is also carried by the front side of the waistband 5, drives ambient air through the hot side 8b of thermoelectric cooling device 8 directly to the atmosphere at the front side of the waistband, as shown by the arrows in FIG. 2, to dissipate the heat generated in the hot side of the thermoelectric cooling device. It will be appreciated that even though the heat is dissipated at the front side of the waistband, it is dissipated at a location distant from the pouch, and therefore distal from the scrotal area of the male user.

FIG. 5 illustrates a modification that may be provided to dissipate the heat generated by the hot side of thermoelectric cooling device 8 even more distant from the scrotal area of the male user. Thus, as shown in FIG. 5, waistband 11 is formed with a passageway 15 communicating with the fan 9b and the hot side 8b of thermoelectric cooling device 8 for directing the heated air to the back side of the waistband and to exit from outlet 16 (FIGS. 6 and 7) directly to the atmosphere. Since outlet 16 is at the back side of the waistband, the discharge of the heat is even more distal from the pouch 2 and the scrotal area enclosed thereby. As shown in FIG. 5, passageway 15 for dissipating the heat generated at the hot side 25 of the thermoelectric cooling device 8 is separated by a partition 17 from the passageway to pouch 2.

Since some heat is also generated in the battery and control circuitry for the thermoelectric cooling device 8, these elements may also be included within passageway 15, as shown at 18 and 19, respectively, in FIG. 5, so as to enable fan 9b also to dissipate the heat generated therein through the outlet 16 of passageway 15 at the back side of the waistband 11.

Figure 8:
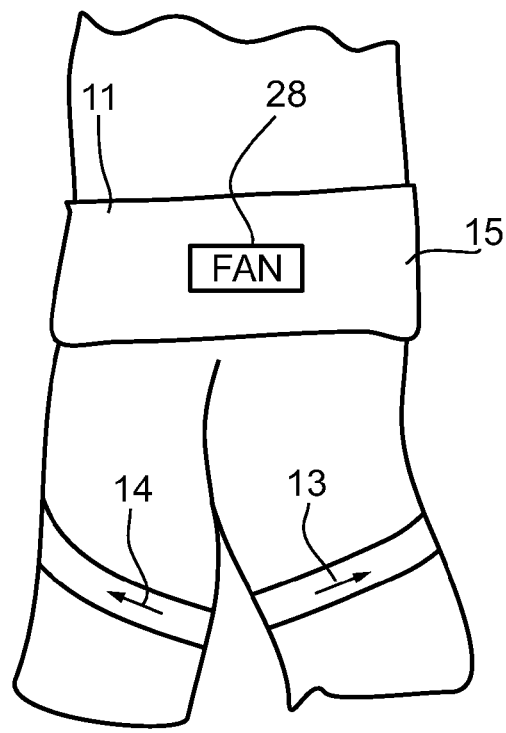
FIG. 8 illustrates a modification in the cooling apparatus of FIGS. 4-6, in that the rear portion of the waistband includes a fan.

FIG. 8 illustrates another alternative which may be used where a higher rate of head dissipation may be needed. In such case, the rear side of waistband 11 may be provided with a fan 28.

Figure 9:
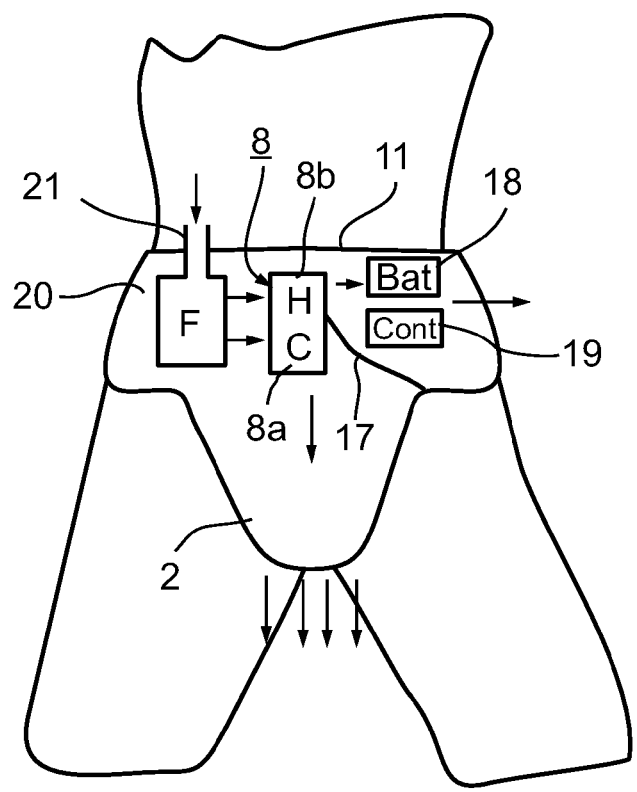
FIG. 9 illustrates a further form of cooling apparatus constructed in accordance with the present invention utilizing ambient air as the cooling fluid rather than a liquid.

FIG. 9 illustrates a further variation wherein the cooling fluid is not a liquid, such as water, but rather is ambient air which is drawn into the waistband, used for cooling the pouch, and then discharged back into the environment. In such a construction, the undergarment 10 could be made of porous fabric as it would not require liquid conduits for conducting a liquid cooling fluid. In this case, waistband 11 may also include the passageway 15 described above with respect to FIG. 5, defining two separate paths, namely the cooling path including the cold end 8a of thermoelectric cooling device 8 and pouch 2, and the heat dissipation path including the hot end 8b of cooling device 8. The latter path also includes the controller 19 and battery 18. A single air pump or fan 20 may be provided to circulate the cooling air through the two above-described paths. It draws air into the waistband via an inlet 21. In many cases, the porous nature of the fabric used for making the waistband would be sufficient to permit the air circulating through the cooling path, after cooling the scrotal area, to be expelled back into the environment at the lower end of pouch 12, and the heated air to be expelled back into the environment at one end of the waistband 11. In some cases, it may be desired to provide conduits for both paths.

Proposed Testing Protocol

Following is a proposed protocol for testing the cooling apparatus and method described herein for reducing risk of male infertility:
Participation
  20 males from 20-35 years of age are to participate.

Criteria for Inclusion
  1. Clinical testing of sperm reduction or damage will be made on all the participants according to World Health Organization Guidelines (WHO) 1999, 2000
  2. All patients will be distinguished by sperm reduction (Varicocele) of Groups II-III after examination by palpation as confirmed by Doppler Ultrasonography of the testicles. In the same imaging examination will be examined the tests, the epididymis, the prostate, and the sperm sac.
  3. The volume of the testicles will be determined by using Prader Orchiometer.
  4. For all the participants, there will be examined the level of FSH, LH and Testosterone before the start of the testing.
Criteria for Exclusion
  1. Sperm density lower than $1 \times 10^6$ ml.
  2. Nicrozosphrmia.
  3. Liquids in volume less than 1 mm.
Period of Testing
  12 weeks.
Description of the Testing Method The males, after examination for reduced or pathological sperm, will be examined by a urologist at the clinic, and to the extent found suitable after the above examination, will receive, without payment, an active cooling system operated by means of chargeable batteries and carried by a waist belt. The unit will be connected by two tubes to the pouch worn on the testicles during the daylight hours from 0800 to 1600 for twelve weeks. In the fourth, eighth and twelfth weeks, an examination of the sperm will be made on all the participants in the same laboratory. Upon the completion of the treatment, an examination will be made by ultrasonography to include a measurement of the volume of the testicles.

While the invention has been described with respect to several preferred embodiments, it will be appreciated that these are set forth merely for purposes of example, and that many other variations, modifications and applications of the invention may be made.

What is claimed is:

1. Cooling apparatus for use by a male to reduce the risk of, and/or alleviate, male infertility, particularly in a heated environment, comprising:
  a waistband to be worn around the waist of the male user;
  a pouch carried by said waistband, said pouch being configured and dimensioned to enclose the scrotal area of the male user;
  a thermoelectric cooling device carried by said waistband, said thermoelectric cooling device having a cold side and a hot side and fluid pumping means carried by said waistband for pumping a first fluid through a cooling path across said cold side of said thermoelectric cooling device to said pouch to cool said pouch and the scrotal area enclosed thereby, and a second fluid through a heat-dissipation path across said hot side of the thermoelectric cooling device to an outlet from said waistband remotely located from said pouch to thereby dissipate the heat produced by said thermoelectric cooling device in cooling said pouch at a location remote from said pouch.

2. The cooling apparatus according to claim 1, wherein said waistband includes a front side carrying said thermoelectric cooling device and said pouch spaced below said thermoelectric cooling device, and a back side in which said outlet of the heat-dissipation path is located.

3. The cooling apparatus according to claim 2, wherein said front side of the waistband also carries said fluid pumping means; and wherein said cooling path, through which the cooling liquid is circulated, includes a conduit from said fluid pumping means to said cold side of the thermoelectric cooling device, a conduit from the cold side of the thermoelectric cooling device to said pouch, and a conduit from said pouch to said fluid pumping means.

4. The cooling apparatus according to claim 3, wherein said pouch includes a further, elongated conduit traversing substantially the complete surface area of the pouch through which the cooling liquid is circulated.

5. The cooling apparatus according to claim 3, wherein said fluid pumping means includes a fan for forcing ambient air over said hot side of the thermoelectric cooling device to dissipate the heat therefrom to the atmosphere via said outlet at the back side of the waistband.

6. The cooling apparatus according to claim 5, wherein said fan is carried by the front side of the waistband to dissipate heat from the front side of the waistband generated in the hot side of the thermoelectric cooling device, as well as in the fan, through said outlet at the back side of the waistband.

7. The cooling apparatus according to claim 1, wherein said fluid pumping means includes a liquid pump for pumping a cooling liquid across the cold side of said thermoelectric cooling device through said cooling path to said pouch, and a fan for pumping ambient air across the hot side of said thermoelectric cooling device through said heat-dissipation path to said outlet in the waistband remotely located from said pouch.

8. The cooling apparatus according to claim 7, wherein said back side of the waistband carries said fan.

9. The cooling apparatus according to claim 1, wherein said fluid pumping means includes a fan for pumping ambient air across the cold side of said thermoelectric cooling device through said cooling path to said pouch, and also across the hot side of said thermoelectric cooling device through said heat-dissipation path to said outlet in the waistband remotely located from said pouch.

10. The cooling apparatus according to claim 1, wherein said waistband and said pouch are incorporated in an undergarment to be worn by the male user.

11. The cooling apparatus according to claim 1, wherein said waistband and said pouch are incorporated in a jock strap to be worn by the user, in which an upper end of the pouch is secured to the front side of the waistband to depend below the waistband, and a lower end of the pouch is secured by leg straps connected to the opposite sides of the waistband.

12. The cooling apparatus according to claim 1, wherein said waistband further carries a battery for powering said thermoelectric cooling device, and a controller for controlling said thermoelectric cooling device.

13. The cooling apparatus according to claim 1, wherein said thermoelectric cooling device is a Peltier device.

* * * * *